United States Patent [19]

Cournut et al.

[11] 4,020,558

[45] May 3, 1977

[54] BUCCAL IMPLANT FOR ADMINISTERING SOLUBILIZABLE PRODUCTS

[75] Inventors: René Cournut, Bordeaux-Cauderan; Gilbert Gaussens, Meudon, both of France

[73] Assignee: Societe Sodermec, Souillac, France

[22] Filed: July 21, 1975

[21] Appl. No.: 597,787

[30] Foreign Application Priority Data

July 19, 1974   France ............................ 74.25254

[52] U.S. Cl. ................................ 32/40 R; 128/260
[51] Int. Cl.² .......................................... A61C 3/10
[58] Field of Search ......... 128/222; 424/14, 15–22; 32/14, 2, 40, 64, 260

[56] References Cited

UNITED STATES PATENTS

| | | | |
|---|---|---|---|
| 3,444,858 | 5/1969 | Russell | 128/260 |
| 3,510,948 | 5/1970 | Walthell | 32/64 |
| 3,888,975 | 6/1975 | Ramwell | 128/260 |

*Primary Examiner*—Robert Peshock
*Attorney, Agent, or Firm*—Sughrue, Rothwell, Mion, Zinn & Macpeak

[57] ABSTRACT

The buccal implant is constituted by at least one plate of small thickness formed of material containing solubilizable substances. The plate is fastened to the teeth and maintained in close proximity to the gum in order to pass the solubilizable substances into the saliva.

11 Claims, 11 Drawing Figures

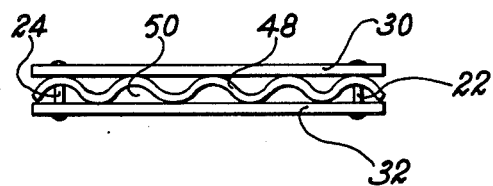
FIG. 8
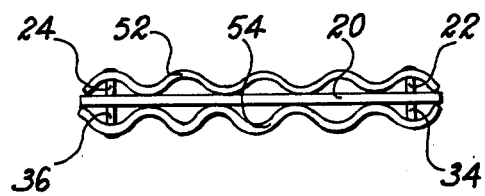
FIG. 9
FIG. 10
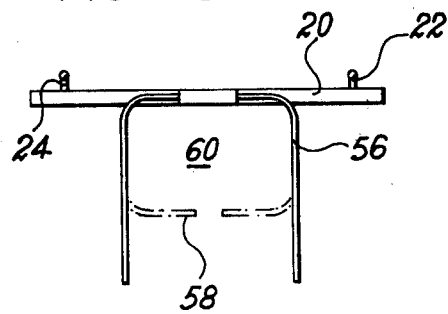
FIG. 11
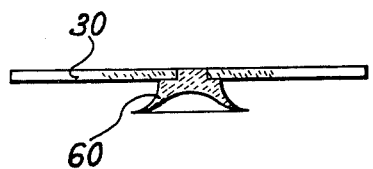

BUCCAL IMPLANT FOR ADMINISTERING SOLUBILIZABLE PRODUCTS

This invention relates to a buccal implant for passing soluble or solubilizable substances contained in said implant into the saliva.

It is known that certain substances, medicaments, analgesics, tranquilizers or the like must be introduced into the human body both continuously and in small doses. When these medicaments are administered through traditional channels such as oral, subcutaneous or the like, this administration is performed abruptly, thus resulting in a variation of large doses of said substances in the body, especially in the case of products which produce rapid metabolization. Thus an excessive dose is given at the outset followed by a more or less rapid decrease according to the rate of injection of the medicament. In the case in which excessive doses of medicaments are unnecessary and even dangerous by reason of their secondary effects, it is necessary to subject the patient to repeated absorptions of small doses. This gives rise to a large number of disadvantages, in particular the possibility of forgetting doses and does not overcome the disadvantages relating to "sawtooth" concentrations in the body. Moreover, it is sometimes an advantage to sweeten the breath continuously by means of an aromatic substance which is continuously fixed in the mouth by means of a mechanical support.

The present invention is directed to a buccal implant of a novel type which releases in a sufficiently uniform manner the substances which are contained therein in order that it can be employed during a period of time of the order of several hours or even several days. The implant is of simple construction without any danger for the mucous membrane of the mouth and is easy to place in position without requiring the presence of a medical practitioner.

Furthermore, said device limits the dangers attendant upon accidental injection of excessive doses of medicament since the plates have a longer active service life. The medical practitioner is able to control the dose given to the patient and to interrupt the injection at any time, which is not the case with pills or tablets which are swallowed and cannot be recovered.

The interdental implant is constituted by at least one plate of small thickness and of suitable shape such as a rectangular shape, for example, said plate being placed in the vicinity of the gum and attached to the teeth by fastening means. The plate is formed of material which contains solubilizable substances. In a preferential embodiment of the invention, the fastening means make use of the interdental space for inserting an element which maintains the plate in position, that is to say opposite to the gum.

Suction cup devices are also employed for attaching the plate, these different devices being intended to ensure that the plate is continuously moistened by the saliva into which the substances of the plate are released. After passing into the saliva, the substances are carried into the body at each deglutition (approximately 1200 per day).

In one embodiment of the invention, the means for fastening the plate are constituted by a spike (or a number of spikes) having the shape of a needle and rigidly fixed to the plate. The spike and the plate are both made of plastic material of a suitable type which is not liable to irritate the gum. The spike is perpendicular to the plate and has a slightly smaller section than the interdental space. The length of the spike is of the same order of thickness as the base of a tooth. The spike is inserted in the same manner as a toothpick between two teeth and preferably two teeth of the lower jaw, the plate being adjacent to the gum.

The section of the spike is a polygon which is adapted to the shape of the base of the interdental cavity. In accordance with the invention sections of triangular or trapezoidal shape in which the large base of the trapezium is located at the lower end of the spike are such that said spike is prevented mechanically from pivoting between two teeth and the plate thus remains in a stationary position after the spike has been fixed. It is also possible to give an adapted curvature to the sides of the triangle constituting a section of the spike so that fastening of this latter between the teeth can be even further facilitated. At the end remote from the plate, there can advantageously be added to the spike a small flexible stud which is substantially perpendicular to said spike and is capable of bending at the time of insertion of the spike between the teeth. Said stud forms a stop for preventing the spike and consequently the plate from slipping in particular towards the front of the mouth.

The spike-stud assembly performs the function of a harpoon. Locking of the device in accordance with the invention between the teeth is perfect; the polygonal shape of the spike prevents any movement of rotation and the stud prevents any movement of translation. In the case of a suction cup associated with the plate and applied either against the gum or against a gum prosthesis, the two movements of locking in translation and in rotation are carried out simultaneously. It is also possible to attach the plate by means of a reinforced wire which is inserted on each side of one or a number of teeth and which can be bent back against the teeth on the side remote from the plate.

It is readily apparent that, in the case of plates of larger size which are intended to release a greater quantity of product into the saliva, it may prove necessary to attach the plate or plates to two spikes which are inserted between two different pairs of teeth.

Tests performed on a large number of patients have shown that the implant did not cause any disadvantages so far as the gum was concerned and permitted ready adaptation since the patient had a tendency to forget his implant after a few minutes. The implant does not cause any hindrance either to breathing or to swallowing, does not cause any irritation and permits smoking, drinking and eating.

The use of the device during the night is not attended by any disadvantages. It is true that deglutition takes place at a lower rate but this very phenomenon can be an advantage for injecting the medicament or any other substance at a smaller nocturnal dose.

The substance constituting the plate can be wholly soluble, with the result that the soluble medicament passes from the plate into the saliva. Alternatively and in accordance with a preferential embodiment of the invention, said substance can be constituted by a hydrophobic substrate containing hydrophilic inclusions in which any desired medicament has been stored. The hydrophobic substrate containing hydrophilic inclusions was described in French patent Application No 73 40002 by Commissariat a l'Energie Atomique and filed on Nov. 9, 1973 in respect of "Hydrophobic substrate containing hydrophilic inclusions." With this substrate, the saliva which moistens the plate passes through the hydrophobic substrate, dissolves part of the substances which have high concentrations in the hydrophilic inclusions; these substances then perfuse through the hydrophoblic substrate so as to be injected into the body by means of the saliva.

It is readily apparent that the dose can be varied and a number of medicaments can even be mixed together by adding a number of plates on a single spike.

In the case of medicaments having a bitter and unpleasant taste which are fixed on a plate, it will be an advantage to add a second plate containing aromatic substances containing menthol, for example, in order to conceal the taste of the medicament.

It will be noted that the plates are usually moistened on both faces, namely the face which is placed against the gum and the other face which is placed in contact with the mucous membrane of the mouth. Tests have shown that the preferential location of the implant was in the vicinity of the first molars close to Stensen's duct which is connected to the parotid gland. However, each person can clearly place the implant between the teeth which have a favorable spacing. After a certain number of dental operations calling for a local analgesic in the vicinity of a tooth, the implant will preferably be placed in the vicinity of this tooth in order to attenuate postoperative pains.

In order to facilitate the manufacture of dental implants, it is sometimes an advantage in accordance with the invention to construct them in two parts; the first part is constituted by one or a number of spikes rigidly fixed to a small cross-bar provided with male studs and a second part constituted by one or a number of plates pierced with holes, the plates being intended to be fixed on the spike by means of the hole which is engaged over the studs.

In another embodiment of the invention which is particularly useful when the medicament is to be stored in the liquid state, there can be included in the plate a cavity filled with liquid containing the substances to be administered, the walls of said cavity being constituted by a plastic hydrophobic material containing hydrophilic inclusions as described earlier. More generally, any membrane which allows the contents located on one side of the membrane to diffuse at a low and uniform rate when placed in contact with water can be employed in order to constitute the walls aforementioned.

It is also possible to store soluble substances in the solid state within the cavity, said substances being dissolved in contact with the saliva which diffuses within the cavity. The difference in osmotic pressure resulting from the dissolved substances causes these latter to migrate with the saliva within the oral cavity in order to be assimilated by the patient. With a view to assisting exchange processes between the saliva and the plate it is possible to increase the exchange surfaces in respect of a substantially equal volume by giving corrugated or recessed shapes to the plates. Similarly, in order to prevent that surface of the plates which is in contact with the cross-bar from remaining inactive since this portion is not in contact with the saliva, a corrugated shape can be given to the cross-bar in accordance with the invention.

Further properties and advantages of the invention will become more readily apparent from the following description of exemplified embodiments which are given by way of explanation and not in any limiting sense, reference being made to the accompanying drawings, in which:

FIG. 8 illustrates an embodiment of the invention comprising a cross-bar of corrugated structure;

FIG. 9 illustrates an embodiment of the invention in which both plates have a corrugated structure;

FIG. 10 illustrates a cross-bar fixed on the gum by means of a reinforced wire which is inserted between the teeth;

FIG. 11 illustrates a plate which is rigidly fixed to a suction cup.

Figure 1:
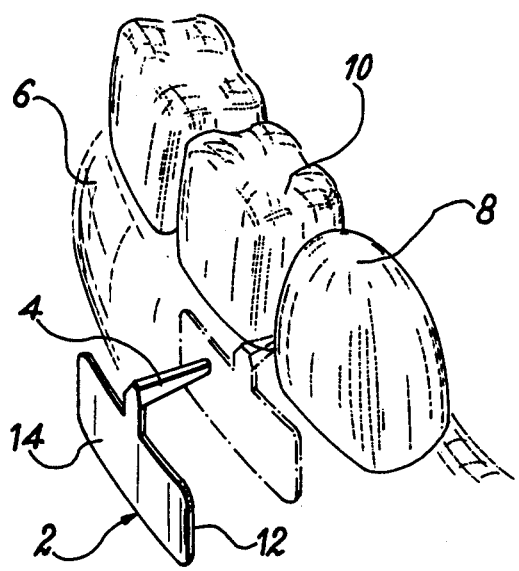
FIG. 1 illustrates an interdental implant placed between two teeth, the plate of said implant being applied against the lower gum.

There is shown in FIG. 1 an interdental implant comprising a plate 2 and a spike 4. Said implant is intended to be fixed on the gum 6 by means of the spike 4 which is inserted between two teeth such as the teeth 8 and 10. The face 12 of the plate is moistened by the gum and the face 14 is moistened by the mucous membrane lining of the mouth.

Figure 2:
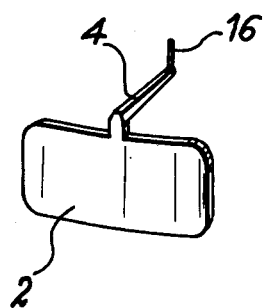
FIG. 2 illustrates an interdental implant provided with a spike and with a stud at right angles to said spike.

In FIG. 2, there is shown an implant of the spike type in accordance with the invention comprising a flexible stud 16 which permits more secure fastening of the implant between two teeth, the stud 16 on the spike 4 being sufficiently flexible to be readily inserted between the two teeth, then to recover its initial shape after insertion so as to lock the dental implant in position. The locking action is produced by the "harpoon effect" which was described earlier.

Figure 3:
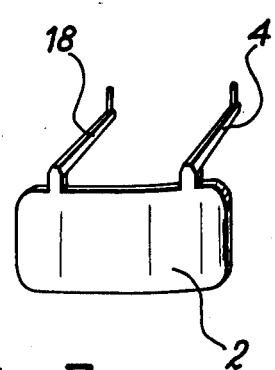
FIG. 3 illustrates an interdental implant provided with two spikes for a single plate.

There is shown in FIG. 3 an interdental implant in accordance with the invention and comprising two spikes 4 and 18 which are attached to a single plate 2.

Figure 4:
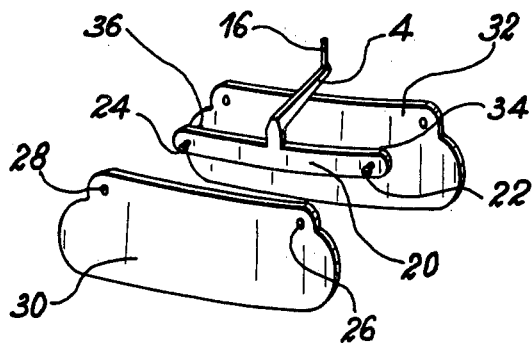
FIG. 4 illustrates an interdental implant made up of three parts, namely two plates and a spike and cross-bar assembly.

FIG. 4 shows an interdental implant made up of two removable portions, namely a spike 4 which is integral with a cross-bar 20 and a plate 30. The plate 30 is provided with holes 26 and 28 which are intended to engage over the studs 22 and 24 of the cross-bar. This device offers a number of advantages: a number of plates can be placed on one side or on each side of the cross-bar on studs such as 34 and 36 which are located on the other side of the cross-bar with respect to the studs 22 and 24, the plate 32 being intended to engage over said studs. This device also makes it possible at the time of treatment of the materials constituting the implant and containing medicaments to separate the plates and to subject only these latter to a physical or chemical treatment without modifying the chemical structure and the mechanical properties of the spike which is constituted by an inert substance usually consisting of plastic.

Figure 5:
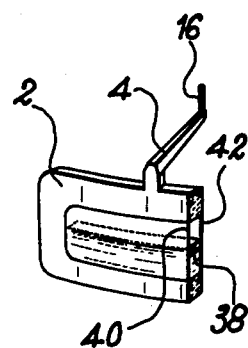
FIG. 5 is a sectional view illustrating an interdental implant provided with a cavity which is filled with a liquid.

FIG. 5 shows an embodiment of the invention in which the plate 2 contains a cavity 38 filled with a liquid 40. The walls such as 42 of the cavity are constituted by a hydrophobic material which contains hydrophilic inclusions, for example and allows the solution to diffuse at a constant rate.

Figure 6:
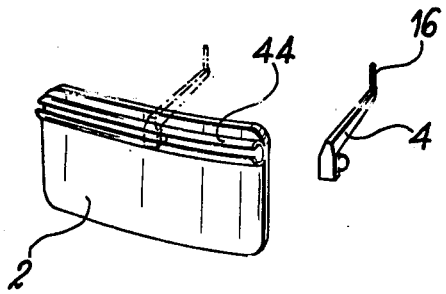
FIG. 6 illustrates an alternative embodiment of the invention.

In FIG. 6, there is shown an alternative embodiment of the invention in which the spike 4 is movable and permits of insertion in the grooved element 44 which is rigidly fixed to the plate 2.

Figure 7:
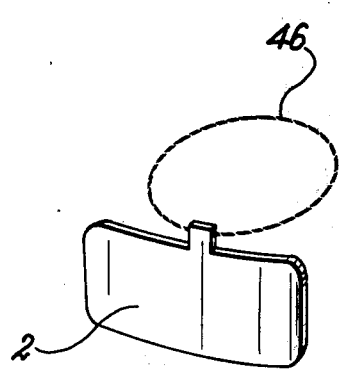
FIG. 7 illustrates an embodiment of the invention comprising a plate and a wire which is inserted between the teeth.

FIG. 7 shows another alternative embodiment of the invention in which the spike is replaced by a wire 46 which surrounds a tooth, the plate 2 being intended to rest on the gum.

The top view of FIG. 8 shows an alternative embodiment of the invention in which provision is made for two plates 30 and 32 fixed by means of the studs 22 and 24 on a crossbar 48 of corrugated shape. The plates 30 and 32 are applied against the cross-bar 48 along generator-lines and allow the saliva to flow within the spaces such as 50. Practically the entire internal surface of the plates is thus moistened by the saliva and desorbs the substances which are included therein.

The top view of FIG. 9 shows a further embodiment of the invention in which provision is made for two plates 52 and 54 of corrugated shape which are attached to the crossbar 20 by means of the studs 22, 24, 34 and 36. These shapes of plates increase the surface area provided for exchange with the saliva.

The embodiment shown in FIG. 10 comprises a crossbar 20 fitted with two studs 22 and 24 on which a plate is intended to be fastened. The fastening means consist of a reinforced wire 56 and preferably a plastic-coated wire which is inserted on each side of a tooth at the base of this latter, said wire being folded back behind the tooth at 58 as shown in chain-dotted lines. The tooth is located within the space 60 which is surrounded by the wire 58.

There is shown in FIG. 11 another mode of attachment of the plates 30 by means of a suction cup 60 which is applied against the gum or against a gum prosthesis.

It is readily apparent that the invention is not limited to the embodiments described and illustrated in the figures but includes on the contrary all the interdental fastening means which serve to maintain the plate against the gum and preferable against the lower gum.

We claim:
1. A buccal implant for passing solubilizable substances contained in said implant into the saliva by maintaining part of the implant close to the gum, wherein said implant is constituted by at least one plate of small thickness formed of material containing solubilizable substances and by means for fastening the plate to the teeth, said means being intended to maintain said plate in the vicinity of the gum.

2. A buccal implant according to claim 1, wherein the means for fastening the plate are constituted by at least one needle-shaped spike placed at right angles to the plate and rigidly fixed thereto, said spike being slightly smaller in section than the interdental space and slightly greater in length than the thickness of a tooth at the base thereof.

3. A buccal implant according to claim 2, wherein the transverse section of the spike is polygonal and especially triangular.

4. A buccal implant according to claim 3, wherein the free extremity of the spike remote from the extremity which is integral with the plate is provided with a small flexible stud substantially at right angles to said spike.

5. A buccal implant according to claim 4, wherein said implant is made up of two removable portions consisting of the spike and the plate, said spike being rigidly fixed to a small cross-bar provided with a plurality of male studs and the plate or plates being provided with holes having dimensions and positions corresponding to the studs of said cross-bar.

6. A buccal implant according to claim 5, wherein the plates have a corrugated surface.

7. A buccal implant according to claim 5, wherein both surfaces of the cross-bar are corrugated.

8. A buccal implant according to claim 1, wherein said implant comprises a suction cup rigidly fixed to the plate.

9. A buccal implant according to claim 1, wherein said implant comprises a reinforced wire of smaller section than the interdental space and securely fixed to the plate.

10. A buccal implant according to claim 9, wherein the plate or plates are constituted by a plastic hydrophobic substrate containing hydrophilic inclusions in which the soluble substances are stored.

11. A buccal implant according to claim 10, wherein the plate or plates are provided with a cavity filled with product, the walls of said cavity being constituted by a substance having controlled permeability.

* * * * *